(12) United States Patent
Steiner et al.

(10) Patent No.: US 8,439,240 B1
(45) Date of Patent: May 14, 2013

(54) CARRIER RACK FOR A VEHICLE

(76) Inventors: Rick E. Steiner, Billings, MT (US); Carson J. Steiner, Elma, WA (US)

( * ) Notice: Subject to any disclaimer, the term of this patent is extended or adjusted under 35 U.S.C. 154(b) by 1035 days.

(21) Appl. No.: 12/182,985

(22) Filed: Jul. 30, 2008

Related U.S. Application Data

(60) Provisional application No. 60/962,737, filed on Jul. 30, 2007.

(51) Int. Cl.
  *B60R 7/00* (2006.01)
  *B60R 9/00* (2006.01)
  *B60P 9/00* (2006.01)

(52) U.S. Cl.
  USPC .................... 224/401; 224/274; 414/462

(58) Field of Classification Search .......... 224/401, 224/274, 409; 414/462
  See application file for complete search history.

(56) References Cited

U.S. PATENT DOCUMENTS

| | | | |
|---|---|---|---|
| 4,061,257 A * | 12/1977 | St. Clair | 224/508 |
| 4,533,013 A | 8/1985 | Hightower | |
| 5,052,604 A | 10/1991 | Tourangeau | |
| 5,236,062 A * | 8/1993 | Laney | 182/127 |
| 5,464,183 A * | 11/1995 | McConnell et al. | 248/311.2 |
| 5,531,478 A * | 7/1996 | Houston et al. | 280/762 |
| 5,595,333 A * | 1/1997 | Boston | 224/536 |
| 5,727,642 A * | 3/1998 | Abbott | 180/65.1 |
| 5,746,364 A | 5/1998 | Stengrim | |
| 5,884,826 A * | 3/1999 | Shaver | 224/509 |
| 6,142,349 A | 11/2000 | Roberson | |
| 6,461,095 B1 | 10/2002 | Puska | |
| 6,705,680 B2 | 3/2004 | Bombardier | |
| 6,902,087 B2 | 6/2005 | Hancock et al. | |
| 7,044,526 B2 | 5/2006 | Tweet et al. | |
| 7,296,959 B2 * | 11/2007 | Davis | 414/462 |
| 2004/0164112 A1 * | 8/2004 | McClain et al. | 224/401 |
| 2005/0045681 A1 * | 3/2005 | Hancock et al. | 224/401 |
| 2007/0023466 A1 * | 2/2007 | Policastro | 224/42.39 |

* cited by examiner

*Primary Examiner* — Nathan J Newhouse
*Assistant Examiner* — Lester L Vanterpool
(74) *Attorney, Agent, or Firm* — Seed IP Law Group PLLC

(57) ABSTRACT

Carrier racks are coupled to a vehicle such that a user can access a pack (e.g., to open and close the pack) carried by the carrier racks. When the vehicle is stationary, items may be loaded and unloaded from the pack while the pack remains securely held by the carrier rack. An all terrain vehicle can include a vehicle frame carrying an engine and a carrier rack fixedly coupled to the vehicle frame. The carrier rack has a longitudinal axis that is substantially parallel to a center plane of the all terrain vehicle. The carrier rack extends upwardly from a rearward end of the vehicle. A longitudinally-extending straddle-type seat is between a handlebar assembly of the all terrain vehicle and the carrier rack such a pack on the carrier rack is positioned directly rearward of a rider.

13 Claims, 13 Drawing Sheets

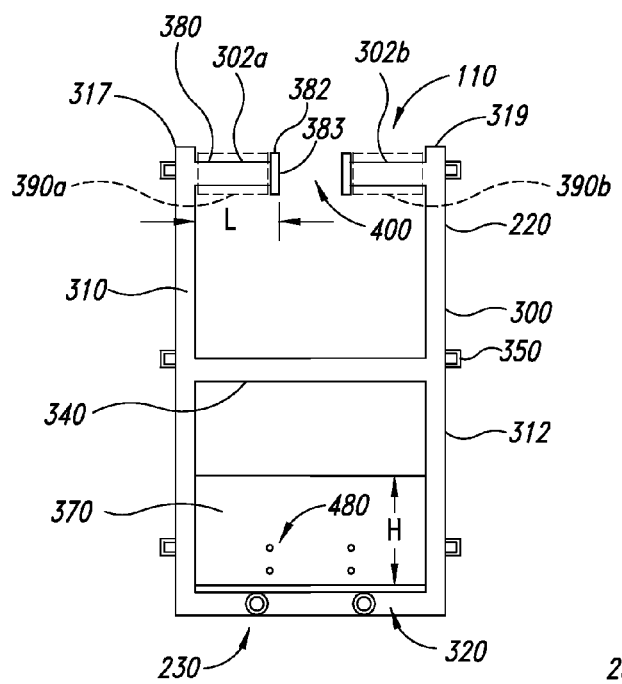
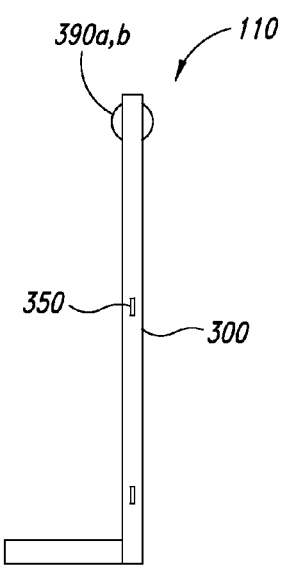
FIG. 5  FIG. 6
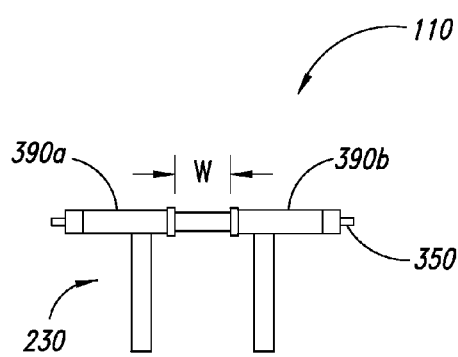
FIG. 7

CARRIER RACK FOR A VEHICLE

CROSS-REFERENCE TO RELATED APPLICATION

This application claims the benefit under 35 U.S.C. §119 (e) of U.S. Provisional Patent Application No. 60/962,737 filed Jul. 30, 2007, which is incorporated herein by reference in its entirety.

BACKGROUND

1. Technical Field

The present disclosure generally relates to a rack for a vehicle, and more specifically to carrier racks for all terrain vehicles.

2. Description of the Related Art

All terrain vehicles (ATVs) are designed for use on all kinds of rough, rocky, and uneven terrain. ATVs may provide access to relatively remote locations for camping, hunting, or performing other outdoor activities. Unfortunately, ATVs are often not capable of carrying a desired amount of equipment. Packs, such as backpacks, are often used to transport equipment. However, if a person wears a backpack while riding an ATV, the backpack can make it difficult to operate the ATV. The backpack can also be uncomfortable to wear, especially if worn for a long period of time. It is therefore difficult for a rider on an ATV to transport a sufficient amount of equipment using a backpack. ATVs may have integrated storage (e.g., a storage compartment under a seat) or a flat cargo rack adjacent to the seat. Unfortunately, these types of storage features have a relatively low storage capacity.

BRIEF SUMMARY

Some embodiments disclosed herein are directed to carrier racks coupleable to vehicles. A pack can be detachably coupled to the carrier rack such that a user can conveniently access the pack (e.g., to open and close the pack). The carrier rack can be permanently or temporarily coupled to a frame or other portion of the vehicle. When the vehicle is parked, items can be conveniently loaded and unloaded from the pack while the pack remains securely held by the carrier rack. If needed or desired, the pack can be quickly and conveniently removed from the carrier rack. If the pack is a backpack, the backpack can be used to hike, hunt, and the like after removing it from the carrier rack.

The carrier rack, in some embodiments, is a cantilevered rack. The rack extends rearwardly from the vehicle for convenient access. In some embodiments, the carrier rack is positioned rearwardly of the rear wheels of the vehicle. The pack is held above the ground and spaced away from the vehicle. In some embodiments, substantially all of the carrier rack is positioned rearwardly of the rear wheels. In some embodiments, an entire rigid pack support (e.g., a pair of elongate rods, a platform, and the like) upon which the pack rests is positioned rearwardly of the rear wheels.

In some embodiments, the carrier rack holds the pack in a substantially vertical orientation and includes upper horizontal supports for engaging shoulder straps of the pack. A lower support is adapted to support the pack when the shoulder straps are positioned around the upper horizontal supports. The pack rests on the lower support while the upper horizontal support holds the main compartment of the backpack against a vertical frame of the rack rigidly connected to the vehicle.

Mounting brackets are used to couple the carrier rack to the vehicle. A mounting plate of the bracket has a plurality of apertures for receiving fasteners. The mounting plate and fasteners securely couple the carrier rack to the vehicle. Such a mounting bracket has a one-piece or multi-piece construction.

In some embodiments, an ATV includes a vehicle frame carrying an engine, at least one front wheel supporting the vehicle frame, a pair of rear wheels supporting the vehicle frame, a handlebar assembly adapted to move the front wheel relative to the vehicle frame, and a carrier rack fixedly coupled to the vehicle. The carrier rack has a longitudinal axis that is substantially parallel to a center plane of the ATV. An angle formed by the center plane and the longitudinal axis is equal to or less than 10° or 5°.

The carrier rack, in some embodiments, includes a rack frame extending upwardly from a rearward end of the vehicle, at least one lower support extending outwardly from the rack frame, and at least one upper strap support extending from the rack frame and positioned with respect to the at least one lower support such that the carrier rack supports a pack when the pack is placed on the at least one lower support and a shoulder strap of the pack is positioned around the at least one upper strap support. The ATV can further include a longitudinally extending straddle-type seat between the handlebar assembly and the carrier rack. In some embodiments, the ATV is a three-wheeled ATV or a four-wheeled ATV.

The carrier rack has a height and a width, which is smaller than the height. The height is measured in a direction of the longitudinal axis of the carrier rack and the width is measured in a direction substantially perpendicular to the longitudinal axis. Such a slender upwardly extending carrier rack is well suited for passing through brush and other foliage without having the carrier rack become caught on foliage. The rack frame can have a shape that is similar to the pack.

In some embodiments, a carrier rack for a motorized vehicle comprises a frame configured to extend upwardly from a vehicle, a pack support coupled to the frame, a shoulder strap retainer, and a plurality of straps. The shoulder strap retainer extends from the frame and is positioned to receive a pair of shoulder straps of a vertically oriented backpack that rests on the pack support when the motorized vehicle is on a level support surface (e.g., a generally level flat road, dirt trail, and the like). The straps are adapted to hold the backpack when the backpack rests on the pack support and is adjacent to the frame. In some embodiments, the straps are vertically spaced from one another.

In yet other embodiments, a method of placing a pack onto a vehicle is provided. The method includes placing the pack onto a carrier rack at a rearward section of a vehicle. The carrier rack includes a frame extending upwardly from the rearward section and a pack support extending outwardly from the frame. One or more shoulder straps of the pack are placed onto a strap retainer coupled to the frame such that the pack is generally vertically oriented while resting on the pack support. The pack is held against the frame using flexible restraints. In some embodiments, each flexible restraint includes one or more straps capable of wrapping around the pack. The flexible restraints can also include one or more buckles, couplers, or the like for coupling sections of the straps together.

BRIEF DESCRIPTION OF THE SEVERAL VIEWS OF THE DRAWINGS

FIG. 5 is a front view of a carrier rack, in accordance with one illustrated embodiment.

FIG. 6 is a side elevational view of the carrier rack of FIG. 5.

FIG. 7 is a plan view of the carrier rack of FIG. 5.

DETAILED DESCRIPTION

Figure 1:
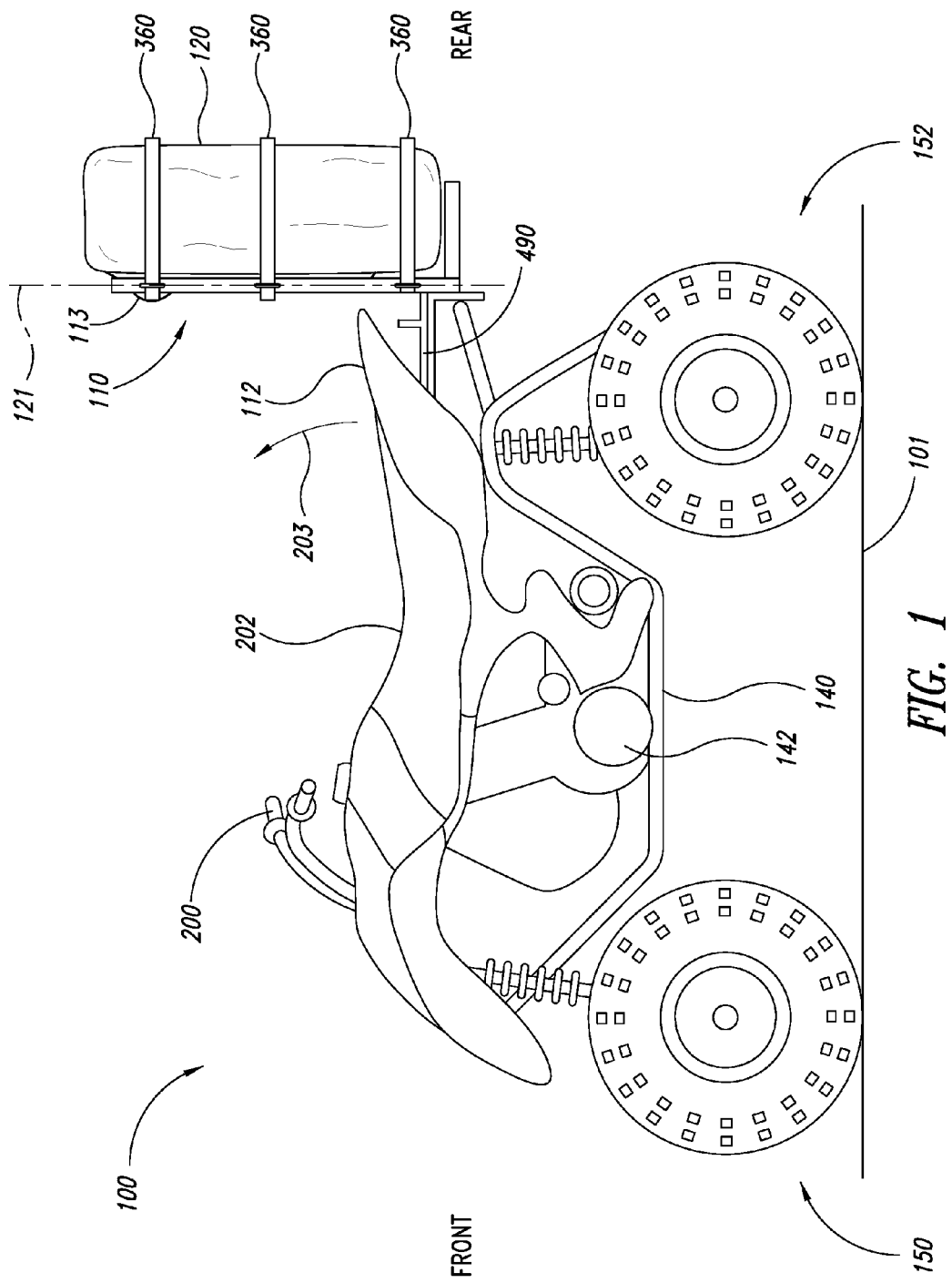
FIG. 1 is a side elevational view of a vehicle and a carrier rack that is holding a pack, in accordance with one illustrated embodiment.
Figure 2:
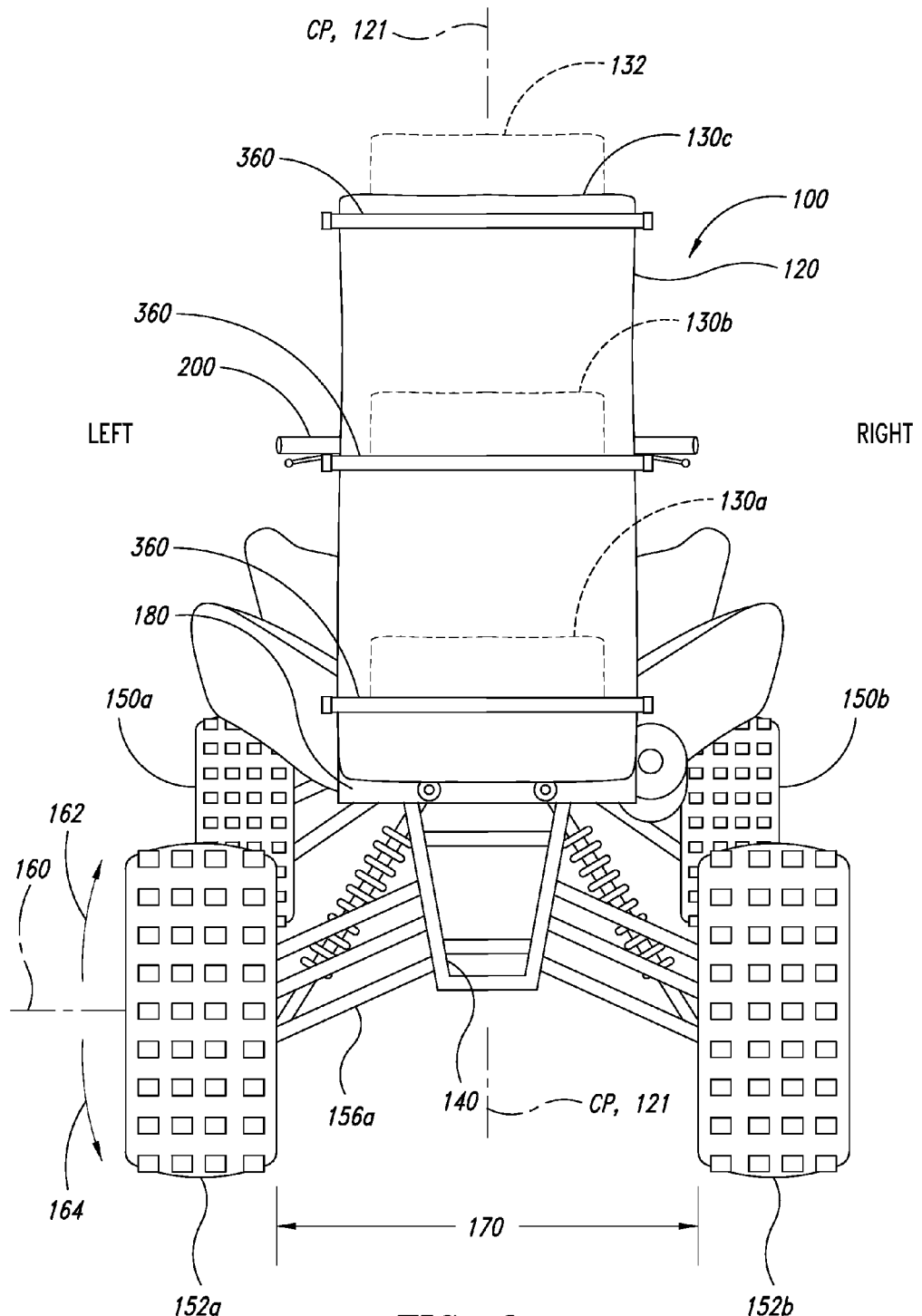
FIG. 2 is a back view of the vehicle and the carrier rack of FIG. 1.

FIGS. 1 and 2 illustrate a vehicle 100 on a level support surface 101 and a carrier rack 110 fixedly coupled to a rearward end 112 of the vehicle 100. The vehicle 100 can travel over all kinds of rough, rocky, and uneven terrain while a pack 120 is securely retained by the carrier rack 110. A user can conveniently access various compartments of the pack 120. The pack 120 can be removed from the carrier rack 110 to transport the pack 120 to other locations that may not be accessible to the vehicle 100. The illustrated carrier rack 110 has a longitudinal axis 121 that is substantially parallel to a center plane of the vehicle 100 to keep the pack 120 upright.

The carrier rack 110 is generally discussed in context with motorized vehicles and holding backpacks because it has particular utility in this context. For example, the carrier rack 110 is particularly well suited for mounting to ATVs and for holding relatively large backpacks with two shoulder straps, such as the shoulder straps 113 in FIG. 1. ATVs can be three-wheeled ATVs, four-wheeled ATVs, or the like and can have low-pressure tires and, in some embodiments, 49 cc to 1000 cc engines. However, the carrier rack 110 can be used in other contexts, such as, for example, on other types of vehicles (e.g., motorcycles, snowmobiles, watercraft, and the like) to hold other types of items, such as travel luggage, suitcases, camping gear (e.g., tents, sleeping bags, etc.), and the like.

Various access locations 130a, 130b, 130c (collectively 130) along the pack 120 provide convenient access to compartments without removing the pack 120 from the carrier rack 110. Because the pack 120 is oriented generally vertically, users can conveniently open one or more of the compartments 130 without allowing any its contents to fall out. For example, an upper flap 132 (shown in dashed line in FIG. 2) at the access location 130c may be opened to gain access to a central main compartment of the pack 120 and closed to prevent any items from falling out when the vehicle 100 travels over rough terrain.

A wide range of different types of packs can be used with the illustrated carrier rack 110. Packs can be, without limitation, backpacks (e.g., frameless backpacks, backpacks with external frames, backpacks with internal frames, or the like) that have at least one shoulder strap wearable on an individual's shoulder. In some embodiments, the backpacks have shoulder harness systems with a pair of shoulder straps. The carrier rack 110 can hold the pack 120 in a substantially vertical orientation using the shoulder straps, even if the pack 120 is completely empty. The empty pack 120 positioned rearwardly of the vehicle 100 can hang from the carrier rack 110 to allow for convenient loading.

The carrying capacity of the pack 120 can be selected based on the cargo to be transported. In some embodiments, the pack 120 has a carrying volume of at least about 30 liters. If the pack 120 is used for camping and hiking, its carrying volume may be at least about 50 liters. In some embodiments, the pack 120 has a carrying volume of at least about 60 liters in order to transport a relatively large cargo. Such packs 120 can be in the form of hiking backpacks or hunting packs with or without frames. Other capacities are also possible, if needed or desired. The pack 120 can also be a duffel, such as a top opening storage duffle or other type of kit bag. Duffels may or may not have shoulder straps. The height H of the carrier rack 110 (FIG. 3) can be equal to or greater than about 60 inches, 40 inches, 36 inches, 30 inches, 24 inches, or ranges encompassing such heights. In some embodiments, the height H is equal to or greater than about 30 inches. The height H of the carrier rack 110 can be selected such that straps of the backpack 120 can be conveniently wrapped over the carrier rack 110.

Most of the carrier rack 110 can be positioned higher than a seat 202 of the vehicle 100. As such, the pack 120 can be positioned directly behind a rider on the vehicle 100.

As used herein, the terms "front," "rear," "back," "left," and "right" and variations thereof refer to directions relative to a rider seated on the seat 202 and facing toward a direction of forward travel of the ATV. However, these directional indications are not intended to limit the embodiments disclosed herein to any particular direction or orientation. The carrier racks and its components disclosed herein may be located or oriented in a variety of desired positions and orientations.

With continued reference to FIGS. 1 and 2, the vehicle 100 includes a vehicle frame 140 carrying an engine 142, a pair of front wheels 150a, 150b (collectively 150) supporting the frame 140, and a pair of rear wheels 152a, 152b (collectively 152) supporting the frame 140 and drivingly coupled to the engine 142. Each of the wheels 150, 152 is coupled to the frame 140 via a suspension system.

The engine 142 can be a V-type engine (e.g., a twin type engine), 4-stroke engine, or 4-cylinder engine, as well as other types of engines which operate on various types of combustion principles (e.g., diesel, rotary, two-stroke, four-cycle, and the like) or having other cylinder configurations, such as in-line, W-type, or horizontally opposed or other numbers of cylinders. The engine 142 can cooperate with a number of systems in order to provide the desired power output. These systems include, without limitation, an induction system, drive train, a fuel system, and an exhaust system, as well as other well known systems and components of ATVs. Various types of drive systems can couple the engine 142 to the rear wheels 152. The engine 142 is positioned generally underneath the seat 202.

FIG. 2 shows a rear left suspension system 156a extending between the frame 140 and the rear left wheel 152a for controlling the travel of the rear left wheel 152a relative to the frame 140. For example, the wheel 152a is rotatable about an axis of rotation 160 while also movable relative to the frame 140 via the suspension system 156a, as indicated by the arrows 162, 164. Various types of known suspension systems can be used to connect the wheels 150, 152 to the frame 140.

The vehicle 100 of FIGS. 1 and 2 further includes a handlebar assembly 200 adapted to move the front wheels 150 relative to the vehicle frame 140. A rider sitting upon the straddle-type seat 202 can rotate the handlebar assembly 200 to steer the vehicle 100. The seat 202 is a generally longitudinally-extending seat positioned between the handlebar assembly 200 and the carrier rack 110. The illustrated seat 202 is positioned rearwardly of the handlebar assembly 200 and positioned forwardly of the carrier rack 110. The straddle-type seat 202 is dimensioned to accommodate a single rider or multiple riders. For example, the seat 202 can be configured to accommodate a driver and at least one passenger seated in a tandem fashion. When the rider straddles the seat 202, the rider can shift the transmission with the rider's left foot, and the rider's right leg is on the other side of the vehicle 100 and can operate a right brake pedal pivotally mounted near a right foot rest.

An access opening or storage compartment may be at least partially arranged beneath the seat 202. For example, the seat 202 or a portion of the seat 202 may cover a compartment such that the seat 202 or the portion of the seat 202 may be removed, or opened about a hinge, to provide easy access to a storage compartment. The compartment can be an engine compartment or other type of compartment, such as a compartment that houses an air cleaner or the like. The illustrated seat 202 can be rotated upwardly, as indicated by an arrow 203 of FIG. 1, to access the compartment beneath the seat 202 while the carrier rack 110 remains coupled to the frame 140.

The illustrated carrier rack 110 is positioned generally above a gap 170 (FIG. 2) between the rear wheels 152. Each of the wheels 152 can travel upwardly with respect to the frame 140 without contacting the carrier rack 110. A lower end 180 of the carrier rack 110 may be positioned below the uppermost portion of the wheels 152 when the wheels 152 are in the fully raised position. The vertical position of the carrier rack 110 can be adjusted based on the track width of the vehicle 100 and characteristics of the suspension systems.

Figure 3:
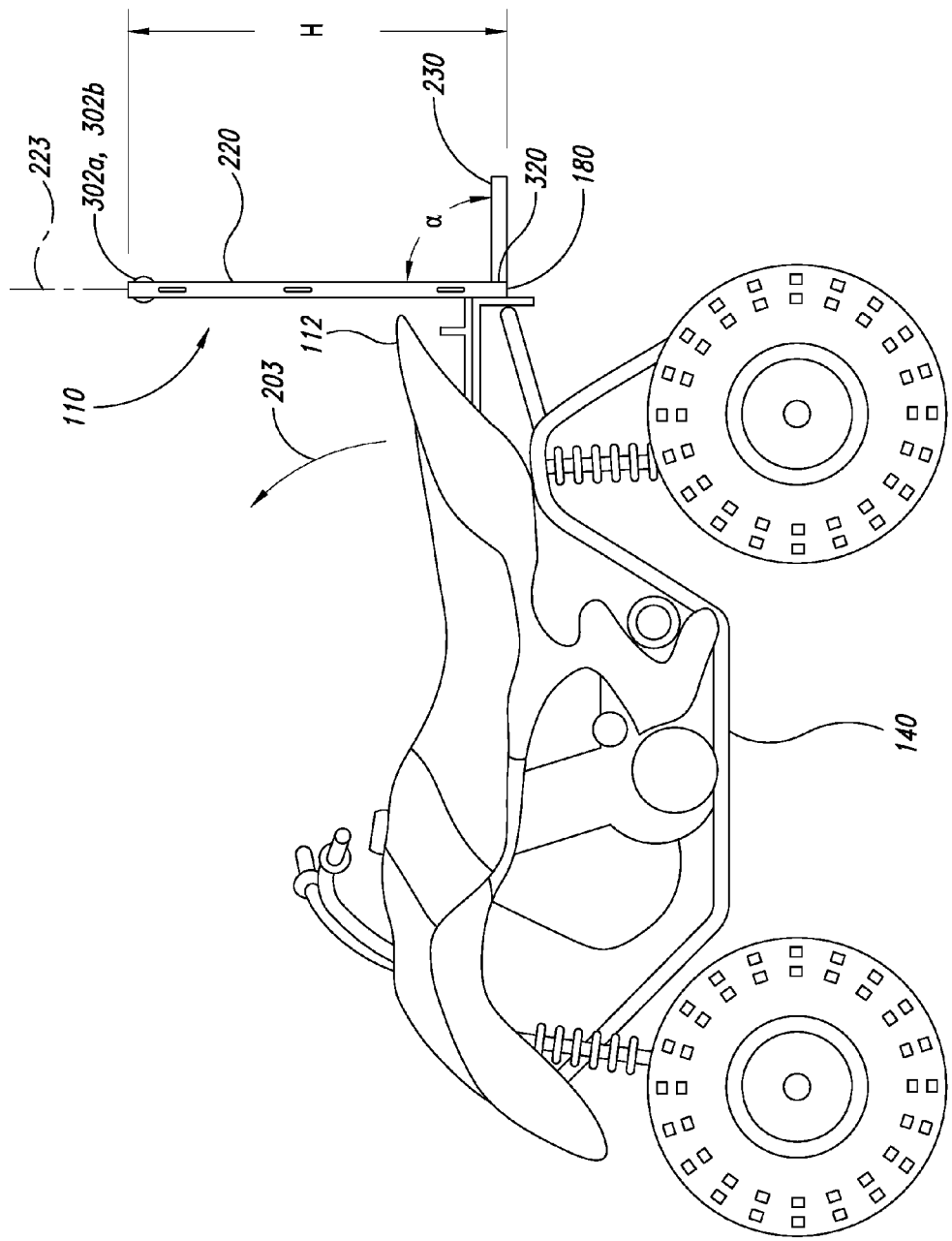
FIG. 3 is a side elevational view of a vehicle and an empty carrier rack.
Figure 4:
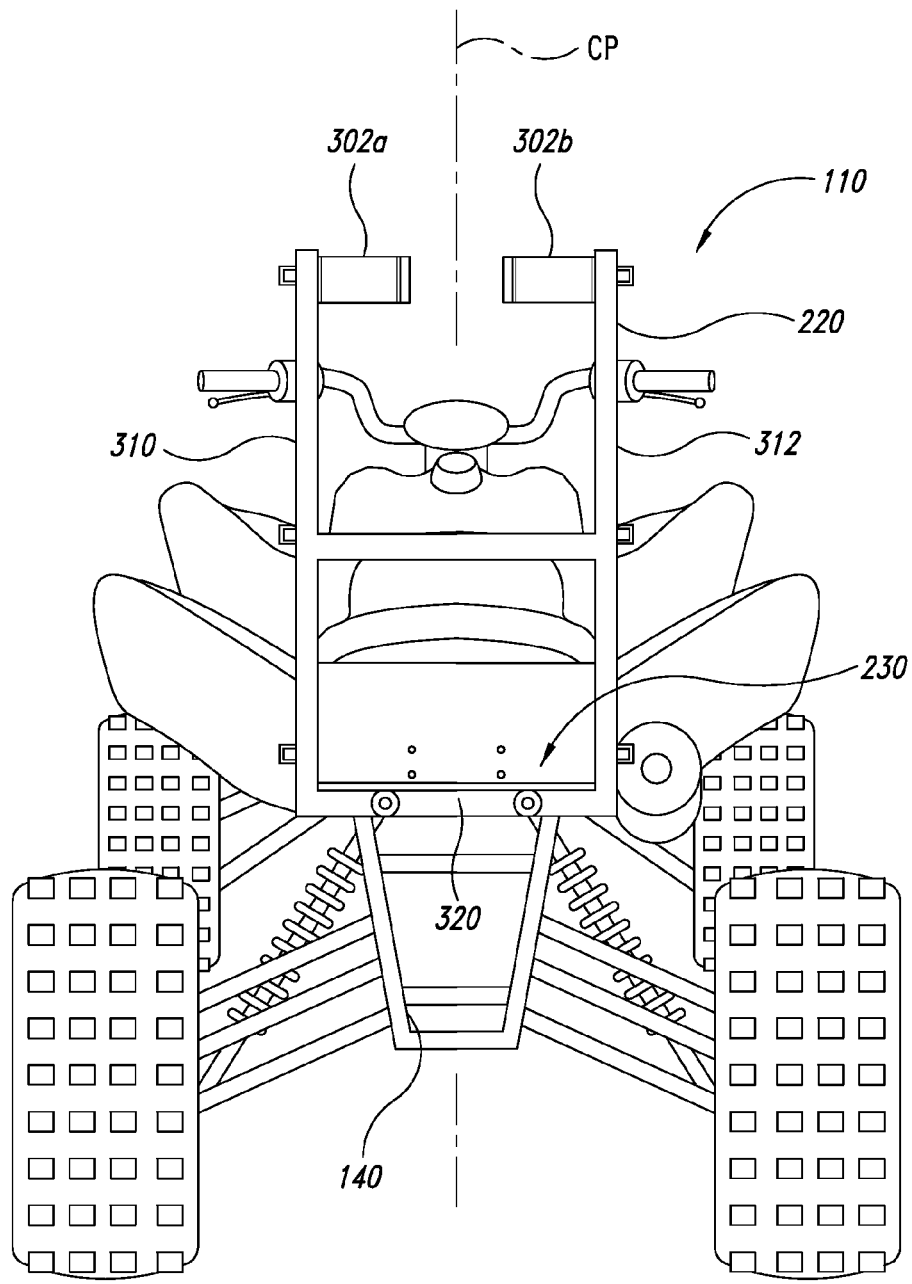
FIG. 4 is a back view of the vehicle and the empty carrier rack of FIG. 3.

Referring to FIGS. 3 and 4, the carrier rack 110 includes a rack frame 220 extending generally vertically upward from the rearward section 112 of the vehicle 100 and a pack support 230 extending outwardly from the rack frame 220. The pack support 230 (illustrated as a pair of elongate spaced apart rods) is positioned with respect to the rack frame 220 such that it supports the pack 120 when one or both of the pack's should straps are positioned around upper strap supports 302a, 302b connected to the rack frame 220. The upper strap supports 302a, 302b are directly above (e.g., vertically aligned with) the pack support 230, as shown in FIG. 4. The rack frame 220 extends a sufficient distance in a direction substantially parallel to the longitudinal axis 121 such that the pack 120 is kept in a generally vertical orientation and is kept from striking any rider on the seat 202. The rack frame 220 includes horizontally spaced apart elongate frame members 310, 312 extending upwardly from a horizontally-extending base 320 to which the lower support 230 is coupled.

The illustrated rack frame 220 is a generally planar frame that extends along an imaginary plane 223 (FIG. 3) and defines an angle α with respect to the pack support 230. In some embodiments, the angle α is in a range of about 80° to about 100° so that the bottom of the pack can rest on the pack support 230 while the pack 120 is held against the rack frame 220. In other embodiments, the angle α can be in a range of about 70° to about 110° or in a range of about 85° to about 95°. Other angles α are also possible, if needed or desired.

FIGS. 5-7 show the carrier rack 110 having a generally rectangular shape. The rack 110 includes the pair of upper strap supports 302a, 302b (collectively 302) rigidly coupled to a U-shaped section 300 of the rack frame 220. The upper strap supports 302a, 302b are coupled to free ends 317, 319 of the elongate members 310, 312, respectively. A reinforcement member 340 extends between the elongate members 310, 312. The illustrated elongate member 310 is generally parallel to the elongate member 312 such that the upper supports 302 are generally aligned with one another. The illustrated upper supports 302 are approximately collinear.

A plurality of vertically spaced apart restraint mounts 350 are fixedly coupled to the U-shaped section 300 such that flexible restraints 360, illustrated as strap assemblies in FIGS. 1 and 2, can be conveniently attached to the rigid U-shaped section 300. The illustrated embodiment includes six U-shaped rigid strap mounts 350. Any desired number of strap mounts can be used.

Each strap assembly 360 can include a flexible strap capable of wrapping around and holding the pack 120 tightly against the rack frame 220. The strap assemblies 360 can also include various types of buckles, fasteners (e.g., hook and loop type fasteners), and other types of connectors for opening and closing.

The rack frame 220 further includes a partition 370 that is positioned between the straddle-type seat 202 and the pack 120. The partition 370 maintains separation between the rider and the pack 120, even if the vehicle 100 rapidly decelerates. The illustrated partition 370 is a rigid plate extending between the elongate members 310, 312 and is positioned slightly higher than the support 230. A height H of the partition 370 can be greater than about 4 inches or 10 inches to ensure that the bottom of the pack 120 does not travel over the partition 370. Other heights H are also possible.

The shoulder strap supports 302a, 302b can be generally similar to each other and, accordingly, the description of one applies equally to the other, unless the context dictates clearly otherwise. The strap support 302a has a substantially linear configuration and has a free end 382 having an end cap 383, an inner tubular body 380, and an outer member 390a (shown in dashed line in FIG. 5) surrounding the tubular body 380. Such linear strap support 302a can be conveniently inserted between a shoulder strap and a main body of the pack 120. As used herein, the term "linear strap support" is broadly construed to include a strap support that extends along a generally straight line. In some embodiments, the linear strap support may be slightly curved or may have other variations in geometry. Of course, the upper strap support can also have a non-linear configuration, if needed or desired. For example, the upper strap support 302a can be a one-piece or multi-piece arm.

A longitudinal length L of the upper strap support 302a can be in a range of about 2 inches to about 12 inches. Such an embodiment is well suited for receiving a shoulder strap of a relatively large pack. In other embodiments, the longitudinal length L is greater than or equal to 4 inches, 6 inches, 8 inches, 10 inches, or ranges encompassing such lengths. Other lengths are also possible. When the rack 110 is installed, the free end 382 can be proximate to (e.g., within 5 inches of) the center plane of the vehicle, as shown in FIG. 4. The length L of the upper strap support 302a can be increased or decreased to decrease or increase, respectively, the distance between the center plane and the end cap 383.

The outer member 390 is captured between the elongate member 310 and the end cap 383 and can cushion the shoulder strap. The outer member 390 may be a compressible tubular member (e.g., a tubular pad) that has a longitudinal length that is generally equal to or slightly smaller than a distance between the elongate member 310 and the end cap 383. In some embodiments, the elongate member 310 and the outwardly protruding end cap 383 can snugly hold the outer member 390 therebetween. The outer member 390, in some embodiments, can be made, in whole or in part, of foam, rubber, compliant plastic, or other suitable highly compliant material for minimizing, limiting, or substantially preventing damage to the pack 120, even if the vehicle 100 travels over extremely uneven surfaces. The outer member 390 serves as a shock absorber to limit damage to the associated shoulder strap. Additionally, grooves, ridges, textured surfaces, or the like can be incorporated into the outer member 390a to minimize, limit, or substantially eliminate unwanted sliding of the shoulder strap.

The outer dimension of the outer member 390 can be less than, greater than, or equal to the outer diameter of the end cap 383. To ensure that a strap remains on the member 390a, the outer member 390a can have an outer diameter that is less than the outer diameter of the end cap 383. The outer member 390a can have a diameter that is generally equal to or greater than the end cap 383 to provide an increased amount of cushion to prevent excessive stresses in the straps of the pack 120.

FIG. 5 also shows a window 400 between the upper strap supports 302. The width W of the window 400 can be equal to or greater than 1 inch, 2 inches, 3 inches, 5 inches, or ranges encompassing such widths. To secure the pack 120 to the rack 110, one strap 113 of the pack 120 can be moved through the window 400 and slid over one of the members 390a, 390b and the other strap 113 can be slid over the opposing member 390a, 390b. In this manner, the straps can be easily secured to the rack frame 220, which in turn holds the pack 120 in an upright position. The straps can remain wrapped around the strap supports 302 until the pack 120 is removed from the carrier rack 110. The upper strap supports 302 can keep the pack 120 from falling off of the support 230, even if one of the straps 360 breaks.

Figure 8:
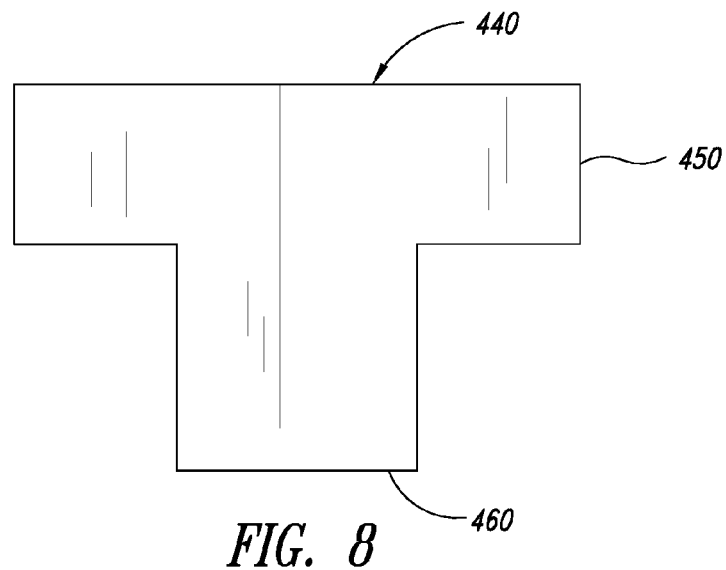
FIG. 8 is a plan view of a mounting bracket for coupling a carrier rack to a vehicle, in accordance with one illustrated embodiment.
Figure 9:
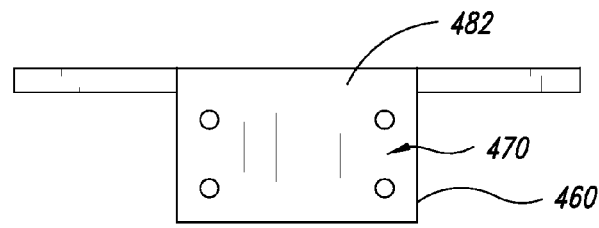
FIG. 9 is a back view of the mounting bracket of FIG. 8.
Figure 10:
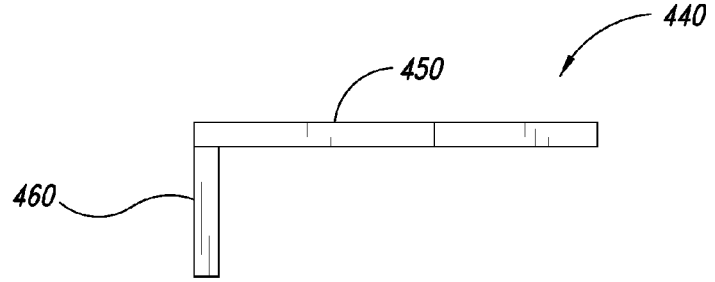
FIG. 10 is a side elevational view of the mounting bracket of FIG. 8.

FIGS. 8-10 illustrate a mounting bracket 440 that includes a vehicle mounting portion 450 and a carrier rack mounting portion 460. The mounting portion 460 extends angularly from the vehicle mounting portion 450. Fasteners can couple the carrier rack 110 to the rack mounting portion 460. For example, fasteners can pass through an array of openings 480 in the plate 370 (FIG. 5) and into corresponding openings 470 in the rack mounting portion 460. As used herein, the term "fastener" is construed to include, without limitation, mechanical fasteners (e.g., nut and bolt assemblies), screws, pins (e.g., pins with cotter pins, self-locking pins, and the like), and the like. In other embodiments, the carrier rack 110 is welded or bonded to the carrier rack mounting portion 460. The mounting bracket 440 can be integrated into the rack frame 220.

Figure 11:
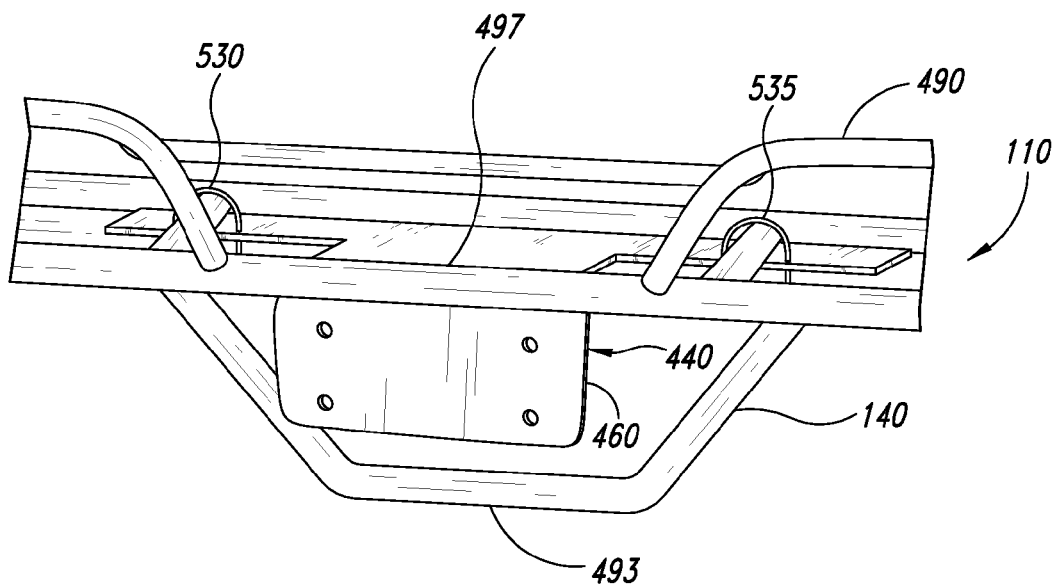
FIG. 11 is a pictorial view of a mounting arrangement to which a frame of a carrier rack can be coupled, in accordance with one illustrated embodiment.

The illustrated carrier rack mounting portion 460 is generally perpendicular to the vehicle mounting portion 450 such that a face of the portion 460 is exposed through the frame 140, as shown in FIG. 11. Each of the openings 480 of the carrier rack 110 can be aligned with one of the openings 470 to allow a fastener to pass therethrough for convenient assembly. When the carrier rack 110 is coupled to the installed mounting bracket 440, the rack frame 220 can overlay the entire carrier rack mounting portion 460.

Figure 12:
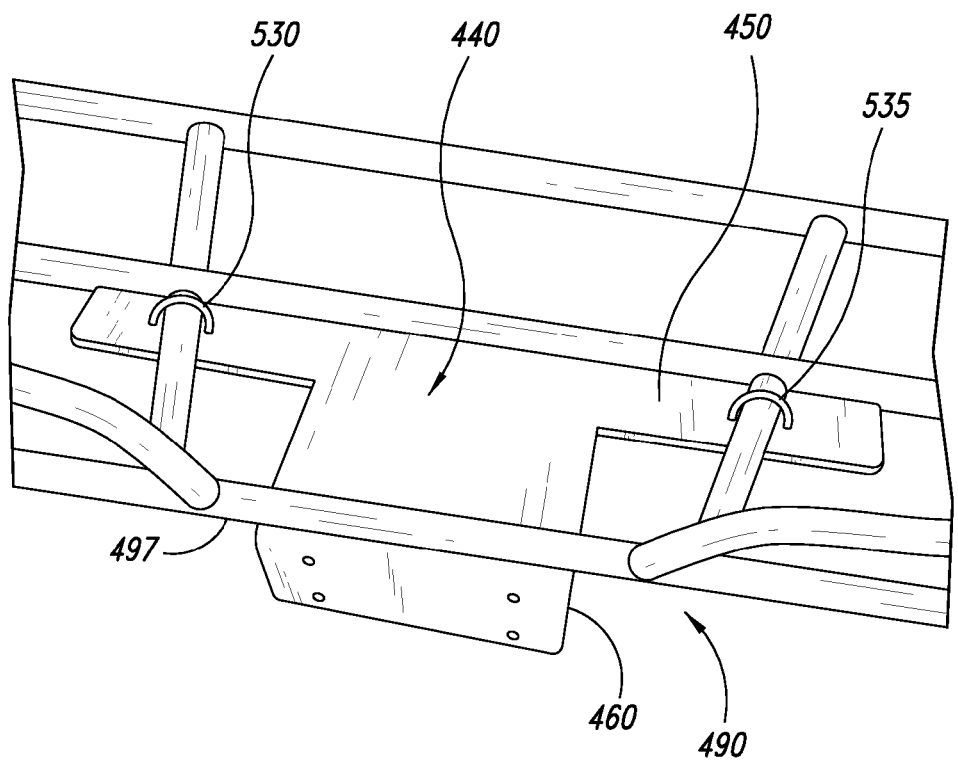
FIG. 12 is another pictorial view of the mounting arrangement of FIG. 11.

FIGS. 11 and 12 illustrate one mounting arrangement in which the mounting bracket 440 is coupled to a rear section 490 of the frame 140. Multiple fasteners 530, 535 securely hold the mounting bracket 440 against the rear section 490 in the form of a cargo rack (see FIG. 1). The carrier rack mounting portion 460 is positioned between a lower bar 493 (shown removed in FIG. 12) and an upper bar 497 of the cargo rack 490.

Figure 13:
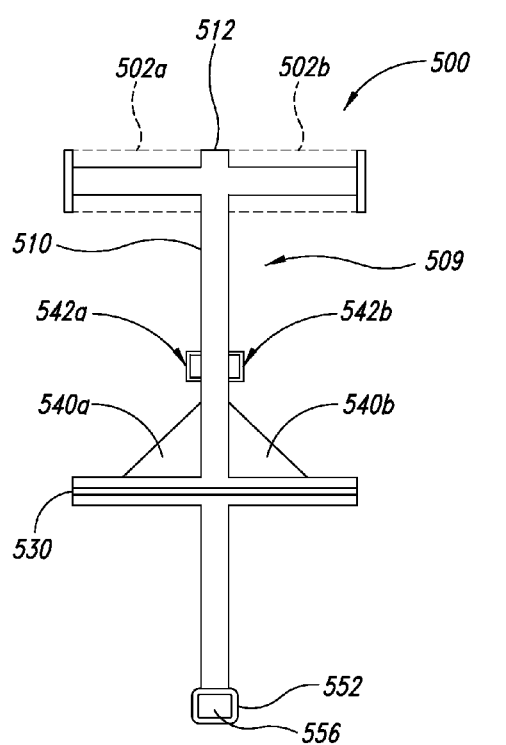
FIG. 13 is a front view of a carrier rack, in accordance with one illustrated embodiment.
Figure 14:
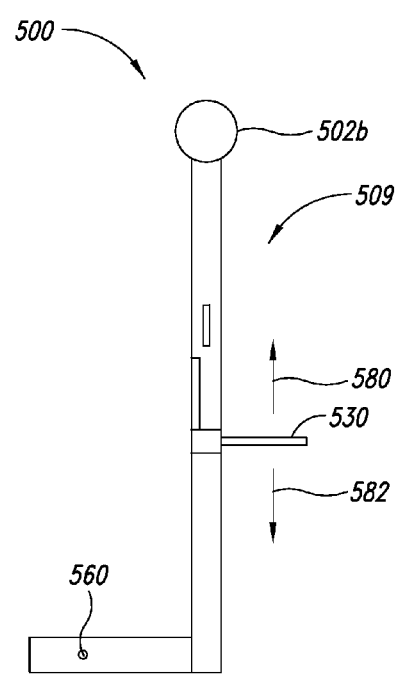
FIG. 14 is a side elevational view of the carrier rack of FIG. 13.

FIGS. 13 and 14 illustrate a carrier rack 500 including a pair of outwardly extending upper strap supports 502a, 502b (collectively 502) and a vertically extending rack frame 509. The rack frame 509 includes an elongate member 510 interposed between the strap supports 502. The illustrated strap supports 502 are coupled at least proximate to an upper end 512 of the elongate member 510. A horizontally extending support 530 (e.g., a pair of rods, a plate, a platform, and the like) extends outwardly from the elongate member 510. Frame reinforcements 540a, 540b (illustrated as gussets) limit, prevent, or substantially eliminate relative movement of the support 530 relative to the elongate member 510. Strap mounts 542a, 542b (collectively 542) are coupled to the elongate member 510. In some embodiments, including the illustrated embodiment, the strap mounts 542 are positioned vertically between the upper strap supports 502 and the lower support 530.

In some embodiments, the support 530 is fixedly coupled to the elongate member 510. In other embodiments, the support 530 can be moved vertically along the elongate member 510, as indicated by the arrows 580, 582 of FIG. 14. The support 530 can be moved vertically to, for example, adjust the vertical position of the pack based on the dimensions of the pack. Various types of locking mechanisms can be used to releasably couple the support 530 to the member 510. These locking mechanisms include, without limitation, spring-loaded pins, pin and cotter pin assemblies, and the like.

The carrier rack 500 is adapted to couple to a receiver of a vehicle. The mount 552 is a generally tubular member insertable into a receiver, such as a hitch receiver of an ATV. FIG. 14 shows an aperture 560 through which a pin or other fastener can be inserted to lock the mount 552 to the receiver.

Figure 15:
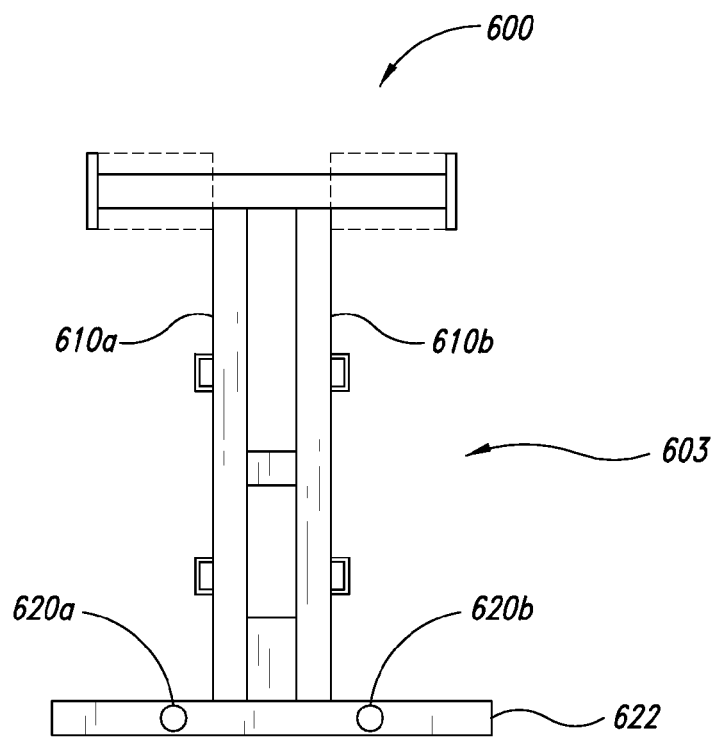
FIG. 15 is a front view of a carrier rack, in accordance with one illustrated embodiment.
Figure 16:
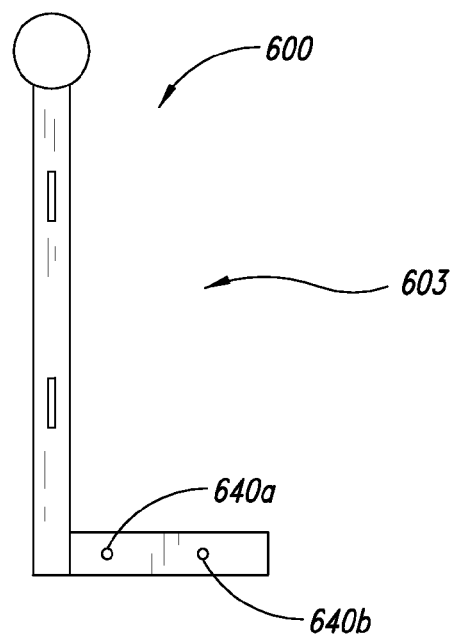
FIG. 16 is a side elevational view of a carrier rack, in accordance with one illustrated embodiment.

FIGS. 15 and 16 illustrate a carrier rack 600 including a rack frame 603 with a pair of vertically extending elongate members 610a, 610b. Lower supports 620a, 620b (collectively 620) are in the form of a pair of elongate rods extending outwardly from a base 622. Each of the lower supports 620 includes a plurality of attachment features, illustrated as openings 640a, 640b, to which accessories can be attached. The other carrier racks discussed herein can also have one or more attachment features, if needed or desired.

Figure 17:
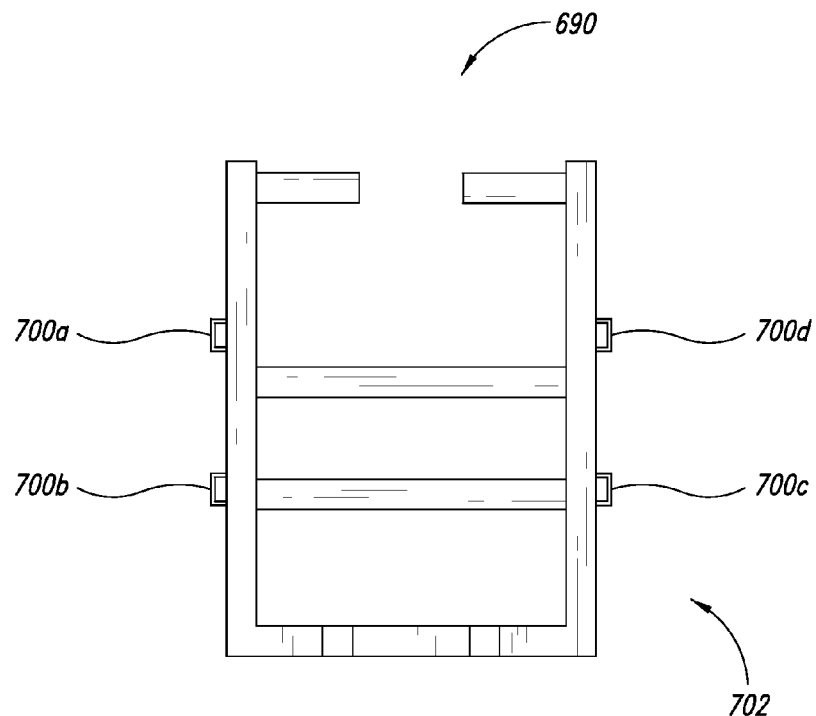
FIG. 17 is a front elevational view of a carrier rack, in accordance with one illustrated embodiment.
Figure 18:
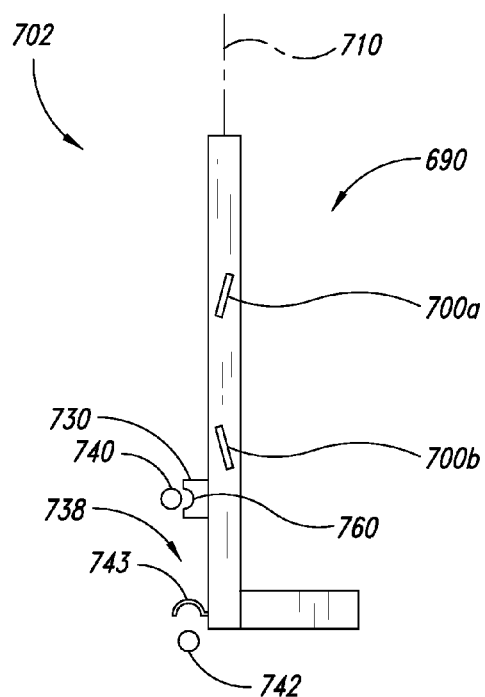
FIG. 18 is a side elevational view of the carrier rack of FIG. 17 adjacent to a portion of a cargo rack of a vehicle.

FIGS. 17 and 18 show strap mounts 700a, 700b, 700c, 700d (collectively 700) that project laterally from a rack frame 702. The angles and positions of the strap mounts 700 can be adjusted based on the desired arrangement of the flexible restraints. The illustrated strap mounts 700 of FIG. 18 are angled with respect to a longitudinal plane 710 along which the frame 702 extends to facilitate crossing of straps that hold the pack.

The carrier racks disclosed herein can be coupled to various types of components of ATVs, such as ATV cargo racks. Spacers, adaptors, and the like can be used to properly orient and position the carrier racks. For example, FIG. 18 illustrates a spacer 730 that positions the frame 702 with respect to an upper cargo rack member 740. The dimensions and configuration of the spacer 730 can be selected based on the desired orientation and position of the frame 702 with respect to an ATV cargo rack. The illustrated spacer 730 has a recess 760 that is brought into contact with and mates to the complementary shaped upper member 740. A hook 743 connected to the frame 702 is placed upon a lower cargo rack member 742. Various types of couplers, fasteners, pins, ties, or other restraints can be used to fixedly couple the spacer 730 and the hook 743 to the members 740, 742, respectively.

FIGS. 19A-21 illustrate a universal mounting bracket 900 capable of adjusting a position of a carrier rack with respect to a vehicle. The extendable bracket 900 can be reconfigured to increase or decrease the distance between the carrier rack and the vehicle. The bracket 900 can also be extended through an opening in a cargo rack or other feature to reach a carrier rack for a convenient installation.

Figure 19A:
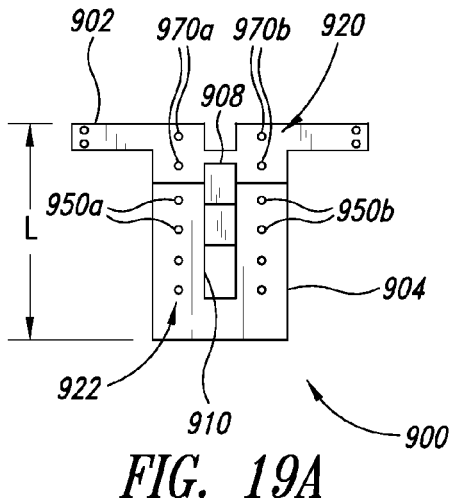
FIG. 19A is a plan view of a multi-piece adjustable mounting bracket, in accordance with one illustrated embodiment.
Figure 19B:
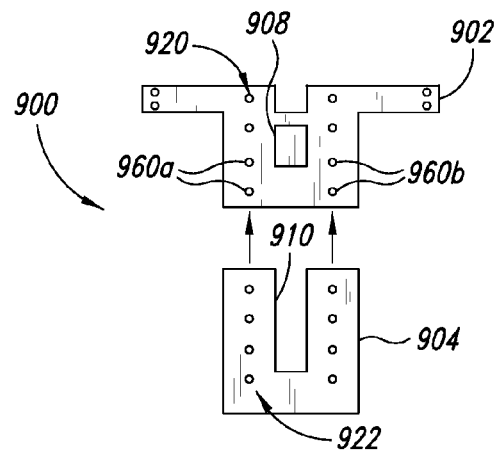
FIG. 19B is a plan view of the mounting bracket of FIG. 19A when a movable member is separated from a stationary member.

The bracket 900 includes a stationary portion 902 and a movable portion 904 that mates with the stationary portion 902. The movable portion 904 can be assembled with the stationary portion 902 by inserting an upwardly protruding guide 908 into a slot 910 of the movable portion 904, as shown in FIG. 19B. The guide 908 and the slot 910 cooperate to limit lateral movement between the portions 902, 904 during and after assembly. Openings 922 of the movable portion 904 can mate with complementary openings 920 of the stationary portion 902. Fasteners are passed through aligned openings 920, 922 to temporarily or permanently couple the portions 902, 904 together.

Figure 20:
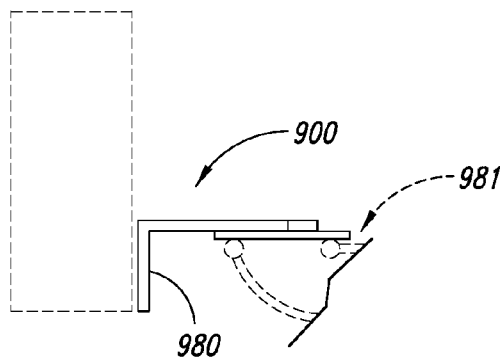
FIG. 20 is a side elevational view of the mounting bracket of FIG. 19A. A pack and a portion of a vehicle are shown in dashed line.
Figure 21:
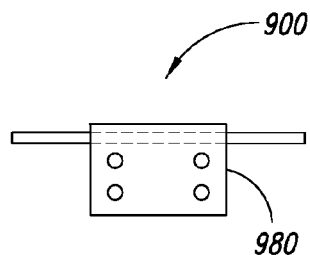
FIG. 21 is a back view of the mounting bracket of FIG. 19A.

A user can align different openings 920, 922 to achieve a desired length L of the bracket 900. For example, to position a carrier rack away from a vehicle, a pair of holes 950a, 950b are aligned with corresponding holes 960a, 960b (FIG. 19B) of the stationary portion 902. To move the carrier rack towards the vehicle, the holes 950a, 950b can be mated with corresponding holes 970a, 970b of the stationary portion 902. In this manner, a downwardly extending coupling plate 980 of the movable portion 904 can be installed at different locations with respect to a vehicle 981 (FIG. 20).

Figure 22:
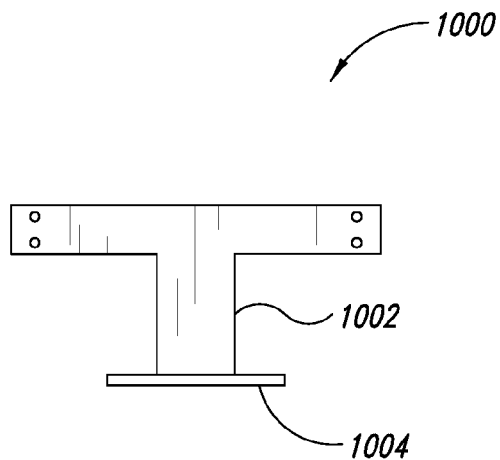
FIG. 22 is a plan view of a mounting bracket that provides different vertical mounting positions for a frame of a carrier rack.
Figure 23:
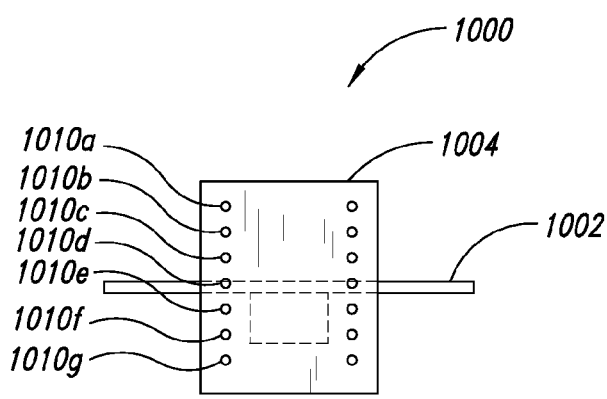
FIG. 23 is a back view of the mounting bracket of FIG. 22.
Figure 24:
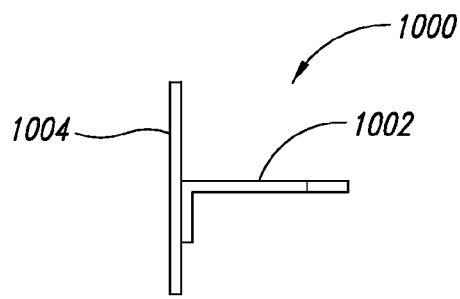
FIG. 24 is a side elevational view of the mounting bracket of FIG. 22.

FIGS. 22-24 illustrate a mounting bracket 1000 that defines a plurality of discrete mounting locations to which a carrier rack can be coupled. The illustrated bracket 1000 includes a vehicle mounting portion 1002 and a vertically oriented coupling member 1004 coupled to the vehicle mounting portion 1002. The vertical coupling member 1004 includes a plurality of vertically aligned openings 1010a to 1010g (collectively 1010). The vertical position of the carrier rack with respect to the ATV can be adjusted by coupling the carrier rack to selected holes 1010. For example, to increase the clearance of the carrier rack, the carrier rack can be coupled to the uppermost pairs of holes 1010a, 1010b. The carrier rack can be coupled to the lowermost pairs of apertures 1010f, 1010g for a reduced clearance. The spacing between adjacent openings 1010 can be selected based on the spacing of the desired vertical mounting positions. For example, the openings 1010 can be evenly or unevenly spaced along the member 1004.

The carrier racks disclosed herein can be in an aftermarket kit. Kits can include a carrier rack, a mounting bracket, packs, and/or fasteners for coupling the mounting bracket to the vehicle and/or coupling the carrier rack to the mounting bracket. The kit can be easily installed on various types of vehicles. These kits can be rapidly installed to increase the carrying capacity of the vehicle without reducing the seating area, performance (e.g., ability to travel over rough terrain), and the like.

It should be noted that, as used in this specification, the singular forms "a," "an," and "the" include plural referents unless the context clearly dictates otherwise. It should also be noted that the term "or" is generally employed in its sense including "and/or" unless the content clearly dictates otherwise.

Various methods and techniques described above provide a number of ways to carry out the invention. Of course, it is to be understood that not necessarily all objectives or advantages described may be achieved in accordance with any particular embodiment described herein. Furthermore, the skilled artisan will recognize the interchangeability of various features from different embodiments disclosed herein. Similarly, the various features and acts discussed above, as well as other known equivalents for each such feature or act, can be mixed and matched by one of ordinary skill in this art to perform methods in accordance with principles described herein. Additionally, the methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof.

The invention claimed is:

1. A method of coupling a pack to an all terrain vehicle, the all terrain vehicle including a vehicle frame carrying an engine; at least one front wheel supporting the vehicle frame; a pair of rear wheels supporting the vehicle frame; a handle bar assembly adapted to move the front wheel relative to the vehicle frame; a carrier rack fixedly coupled to the vehicle frame, the carrier rack including a frame base that extends in a first direction, a pair of elongate frame members that are spaced apart in the first direction and that extend in a second direction, perpendicular to the first direction, from the frame base, at least one lower support extending outwardly from the frame base, an upper strap support portion positioned with respect to the at least one lower support such that the carrier rack supports a pack when the pack is placed on the at least one lower support and shoulder straps of the pack are positioned on the upper strap support portion, and a partition plate extending between the elongate frame members, above the lower support, and below the upper strap support portion, the partition plate being positioned to maintain separation between a rider on the all terrain vehicle and the pack during operation of the all terrain vehicle when the pack is supported by the carrier rack; and a longitudinally-extending straddle-type seat between the handle bar assembly and the carrier rack, the method comprising:

placing a pack onto the carrier rack; and placing the shoulder straps of the pack onto the upper support portion such that the pack is vertically oriented while the pack rests on the at least one lower support.

2. A carrier rack for a motorized vehicle, comprising:
a frame configured to extend upwardly from a rear end of the vehicle, the frame extending vertically from a horizontally extending base and terminating at a U-shaped section, the U-shaped section being defined by an upper portion of a pair of elongate frame members that extend vertically from the base and a horizontally extending reinforcement member;
a pack support coupled to the frame at the base;
a pair of shoulder strap retainers extending horizontally from free ends of the elongate frame members, the shoulder strap retainers positioned to receive a pair of shoulder straps of a vertically oriented backpack that rests upon the pack support when the motorized vehicle is on a level support surface;
a partition plate extending between the elongate frame members, above the base, and below the reinforcement member; and
a plurality of strap holders configured to receive straps that hold the backpack that rests on the pack support and that is adjacent to the frame, the plurality of strap holders including a pair of strap holders on each one of the elongate frame members, one of the pair of strap holders being vertically aligned with the partition plate, and the other of the pair of strap holders being adjacent to the reinforcement member.

3. The carrier rack of claim 2, wherein the carrier rack has a longitudinal axis, the frame extends a sufficient distance in a direction parallel to the longitudinal axis such that the shoulder strap retainer keeps a pack aligned with a center plane of the motorized vehicle.

4. The carrier rack of claim 2, wherein a substantial portion of the frame extends along an imaginary plane and the lower support extends perpendicularly from the rack frame.

5. The carrier rack of claim 2, wherein the pack support projects outwardly from the frame.

6. The carrier rack of claim 2, further comprising a mounting bracket for coupling to a vehicle.

7. The carrier rack of claim 2, further comprising means for coupling the frame of the carrier rack to a vehicle.

8. The carrier rack of claim 7, wherein the means for coupling includes a mounting bracket and at least one fastener for engaging both the frame of the carrier rack and the vehicle.

9. A method of placing a pack onto a carrier rack coupled to a vehicle, comprising:
placing a pack onto a carrier rack at a rearward section of the vehicle, the carrier rack includes a frame extending upwardly from the rearward section and a pack support extending outwardly from the frame;
placing a pair of shoulder straps of the pack onto a strap retainer coupled to the frame such that the pack is vertically oriented while the pack rests on the pack support; and
holding the pack against the frame using a plurality of vertically spaced apart flexible restraints coupled to the frame, the plurality of flexible restraints including a first flexible restraint vertically aligned with a partition plate that extends between vertically extending elongate members of the frame and a second flexible restraint positioned vertically between the first flexible restraint and the strap retainer.

10. The method of claim 9, wherein the placing of the pair of shoulder straps includes passing the pair of shoulder straps through a window defined by the strap retainer such that the strap retainer is between the pair of shoulder straps and a main body of the pack.

11. The method of claim 10, wherein the strap retainer includes a first elongate arm spaced apart from a second elongate arm of the strap retainer to define the window.

12. The method of claim 9, wherein holding the pack against the frame using flexible restraints includes wrapping a plurality of straps about the pack.

13. The method of claim 9, wherein most of the pack is higher than a straddle-type seat of the vehicle when the pack is held against the frame.

* * * * *